US008821437B2

(12) United States Patent
de Costa et al.

(10) Patent No.: US 8,821,437 B2
(45) Date of Patent: Sep. 2, 2014

(54) PHARMACEUTICAL DEVICE FOR THE ADMINISTRATION OF SUBSTANCES TO PATIENTS

(75) Inventors: Samodh de Costa, Cambridge (GB); Bruce Roser, Cambridge (GB); Shevanti Sen, Cambridge (GB)

(73) Assignee: NOVA Bio-Pharma Technologies Limited (GB)

( * ) Notice: Subject to any disclaimer, the term of this patent is extended or adjusted under 35 U.S.C. 154(b) by 1391 days.

(21) Appl. No.: 12/094,581

(22) PCT Filed: Nov. 21, 2006

(86) PCT No.: PCT/GB2006/050403
§ 371 (c)(1),
(2), (4) Date: May 21, 2008

(87) PCT Pub. No.: WO2007/057717
PCT Pub. Date: May 24, 2007

(65) Prior Publication Data
US 2008/0294100 A1    Nov. 27, 2008

(30) Foreign Application Priority Data
Nov. 21, 2005    (GB) .................................. 0523638.5

(51) Int. Cl.
*A61M 5/14*    (2006.01)
*A61K 9/00*    (2006.01)
*A61M 5/28*    (2006.01)
*A61M 5/31*    (2006.01)
*A61M 5/32*    (2006.01)

(52) U.S. Cl.
CPC ............ *A61K 9/0019* (2013.01); *A61M 5/1409* (2013.01); *A61M 5/284* (2013.01); *A61M 5/3145* (2013.01); *A61M 5/3293* (2013.01)
USPC ............................. 604/84; 424/484; 427/2.28

(58) Field of Classification Search
CPC .................................................. A61M 5/1409
See application file for complete search history.

(56) References Cited

U.S. PATENT DOCUMENTS

| 3,244,595 A |   | 4/1966 | Feigh |
|---|---|---|---|
| 4,832,952 A |   | 5/1989 | Hesh et al. |
| 4,874,366 A | * | 10/1989 | Zdeb et al. ..................... 604/518 |
| 4,891,319 A | * | 1/1990 | Roser ............................ 435/188 |
| 5,049,139 A |   | 9/1991 | Gilchrist |
| 5,510,115 A | * | 4/1996 | Breillatt et al. ............... 424/473 |
| 5,531,683 A |   | 7/1996 | Kriesel et al. |
| 5,582,907 A | * | 12/1996 | Pall ............................... 442/351 |
| 6,039,872 A | * | 3/2000 | Wu et al. ................. 210/500.35 |
| 6,190,701 B1 |   | 2/2001 | Roser et al. |
| 6,290,991 B1 |   | 9/2001 | Roser et al. |
| 6,309,671 B1 |   | 10/2001 | Foster et al. |
| 6,468,782 B1 |   | 10/2002 | Tunnacliffe et al. |
| 6,517,860 B1 |   | 2/2003 | Roser et al. |
| 6,565,871 B2 |   | 5/2003 | Roser et al. |
| 6,630,169 B1 |   | 10/2003 | Bot et al. |
| 6,669,963 B1 |   | 12/2003 | Kampinga |
| 6,811,792 B2 |   | 11/2004 | Roser et al. |
| 6,872,357 B1 |   | 3/2005 | Bronshtein et al. |
| 6,964,771 B1 |   | 11/2005 | Roser et al. |
| 7,744,925 B2 |   | 6/2010 | Roser et al. |
| 7,780,991 B2 |   | 8/2010 | Roser et al. |
| 7,785,631 B2 |   | 8/2010 | Roser et al. |
| 2001/0038858 A1 | * | 11/2001 | Roser et al. .................... 424/488 |
| 2001/0055617 A1 |   | 12/2001 | Mattern et al. |
| 2002/0155129 A1 |   | 10/2002 | Roser et al. |
| 2003/0068354 A1 | * | 4/2003 | Reif et al. ...................... 424/423 |
| 2003/0180283 A1 |   | 9/2003 | Batycky et al. |
| 2003/0202978 A1 |   | 10/2003 | Maa et al. |
| 2003/0215515 A1 |   | 11/2003 | Truong-Le et al. |
| 2004/0180827 A1 |   | 9/2004 | Chen et al. |
| 2008/0026066 A1 |   | 1/2008 | Roser |
| 2009/0208585 A1 |   | 8/2009 | Roser et al. |
| 2010/0114014 A1 |   | 5/2010 | Roser |

FOREIGN PATENT DOCUMENTS

| AU | 2005203369 | 8/2005 |
|---|---|---|
| DE | 19903876 A1 | 8/2000 |
| EP | 0913178 | 5/1999 |
| GB | 2413075 | 10/2005 |
| JP | H9-510461 | 10/1997 |
| JP | H11-506467 | 6/1999 |
| JP | 2002-542926 | 12/2002 |
| WO | WO 95/25546 | 9/1995 |

(Continued)

OTHER PUBLICATIONS

Annear, "Recoveries of bacterial after drying in Glutamate and other substances," Aust J Exp Biol Med Sci, Dec. 1964, vol. 64, pp. 717-722.
Hutter et al., "Spray Drying of the Dehalogenating Bacterium *Rhodococcus* sp," Bioprocess and Biosystems Engineering, Springer Verlag, DE, Jan. 1995, vol. 13(1), pp. 19-21.
Pourrat et al., "Stabilization of Octastatin(R), a Somatostatin Analogue. Preparation of Freeze-Dried Products for Parenteral Injection," Biol. Pharm. Bulletin, 1995, vol. 18(5), pp. 766-771.
Foam, "Foam Definition", accessed from: www.chemistry.about.com/od/chemistryglossary/g/Foam-Definition.htm, accessed on Feb. 1, 2012 in U.S. Appl. No. 12/065,493, 1 page.

(Continued)

*Primary Examiner* — Daniel Sullivan
*Assistant Examiner* — Peter Anthopolos
(74) *Attorney, Agent, or Firm* — Sheridan Ross, P.C.

(57) ABSTRACT

Biological materials such as vaccines can be stabilized in certain glassy materials soluble in water. It has been proposed to form these glassy materials as a powder suspended in a non-aqueous liquid for injection into a patient. This method is complicated by the need to find suitable compatible liquids and to stop the glassy particles from congregating in liquid. These problems have been obviated by supporting the glassy material on a porous membrane remote from the eluant. When the biological material requires administration, the eluant can be passed across the membrane dissolving the glass and causing the substance to be carried by the liquid into the patient.

12 Claims, 3 Drawing Sheets

(56) References Cited

FOREIGN PATENT DOCUMENTS

| WO | WO 96/40077 | 12/1996 |
|---|---|---|
| WO | WO 98/41188 | 9/1998 |
| WO | 9843611 A1 | 10/1998 |
| WO | WO 9947174 A1 * | 9/1999 |
| WO | 0032402 A | 6/2000 |
| WO | 0066086 A | 11/2000 |
| WO | WO 00/66256 | 11/2000 |
| WO | WO 00/72827 | 12/2000 |
| WO | WO 00/78924 | 12/2000 |
| WO | WO 02/07813 | 1/2002 |
| WO | WO 02/12289 | 2/2002 |
| WO | 0232402 A1 | 4/2002 |
| WO | WO 02/066005 | 8/2002 |
| WO | WO 2005/099669 | 10/2005 |
| WO | WO 2007/026180 | 3/2007 |
| WO | WO 2007/039769 | 4/2007 |

OTHER PUBLICATIONS

Bosquillon et al., Aerosolization properties, surface composition and physical state of spray-dried protein powders, Journal of Controlled Release, vol. 99, 2004, pp. 357-367 (Abstract) 1 page.

Yu et al., "Preparation and characterization of microparticles containing peptide produced by a novel process: spray freezing into liquid", European Journal of Pharmaceutics and Biopharmaceutics, vol. 54(2), 2002, pp. 221-228 (Abstract) 1 page.

Carvalho et al. "Protective effect of sorbitol and monosodium glutamate during storage of freeze-dried lactic acid bacteria," Le Lait, May-Jun. 2003, vol. 83, No. 3, pp. 203-210.

Mülhausen, Dorothée, Authorized officer, International Bureau of WIPO, International Preliminary Report on Patentability, report issuance date: May 27, 2008.

U.K. Intellectual Property Office, Patents Act 1977: Search Report under Section 17(5), U.K. Patent Application No. GB0623178.1; search date: Aug. 9, 2007.

* cited by examiner

*13.5 micro grams loaded = European Pharmacopoeia acceptable limits of 10 micro grams required

PHARMACEUTICAL DEVICE FOR THE ADMINISTRATION OF SUBSTANCES TO PATIENTS

This invention relates to a pharmaceutical device for the administration of substances to patients. Many pharmaceutical substances are carried in aqueous solution or suspension and, because of the presence of water, must be refrigerated to prevent them from deteriorating.

There is an interest in developing a method of storing, transporting and administering vaccines without the need for refrigeration. One branch of research has focused towards the use of glassy materials which have been shown to have a potential to preserve vaccines at ambient and elevated temperatures, and against freezing for extensive periods of time.

A serious difficulty with this approach is the need to re-dissolve the solid glassy materials in water immediately before use so as to enable their injection into the body. This is fraught with hazard because the wrong quantity of liquid may be used resulting in incorrect dosage being given to patients. With some vaccines e.g. measles, the vaccine becomes very unstable immediately after it is re-hydrated, having a shelf life of only a few hours. If left longer than this it is inactive in patients and does not protect against disease. Also the re-constituting liquid may not be sterile and lead to serious and occasionally even fatal infection of recipients. What is needed is a stable form of vaccine that is either automatically and correctly reconstituted for injection or a stable liquid form that is instantly injectable without re-constitution.

One previously proposed technique is to suspend water soluble glass particles, in which an active material is stabilised, in a non-aqueous carrier liquid as described by Roser & Garcia de Castro in WO 0232402. However, this method has been hindered by problems associated with finding and manipulating both the carrier liquid and the glassy material so as to create a permanent suspension that is capable of passing through a hypodermic needle and that is safe to dispense to patients.

US2003/0068354 A1 (Reif) describes a vaccination device specifically for the injection of genetic material vaccines. The genetic material is chemically bonded onto an anion exchange membrane and then is preserved by freeze drying. To remove the material from the membrane, a buffer solution is used which preferentially removes the genetic material from the membrane leaving it free to be carried in the eluant.

The above system takes advantage of the inherent stability of genetic material, which can be freeze dried with relative ease. Its functionality is also reliant on the relatively low bonding capacity of genetic material so that lower power buffers can be used. However, the above system is not appropriate for the delivery of more thermally labile materials such as protein or virus vaccines which will denaturalise within a few hours if not adequately preserved and are far less adaptable to freeze drying processes.

Further, the bonding strength of proteins to an ion exchange membrane, is in many cases, likely to be much greater than for genetic material. Thus to remove a protein vaccine from an ion exchange membrane would require the use of powerful chemical buffer solutions which could be potentially harmful if administered into infants.

Additionally, ion exchange membranes are wholly unsuitable for use with glassy materials which inhibit the formation of chemical bonding of the vaccine to the ionic exchange membrane and would additionally cause blocking of the pores of the membrane inhibiting the flow of eluant.

The invention provides a pharmaceutical device comprising: means defining a path for the flow of a carrier liquid to a patient, a pharmaceutical material stabilised in a glassy substance and arranged to be carried in the carrier liquid along the flow path to the patient, characterised in that: the glassy substance is formed as a coating on a supporting surface; the supporting surface is exposed to the said flow path of the liquid; and the glassy substance is soluble in the liquid so that it dissolves, thereby releasing the pharmaceutical material into the liquid before entering the patient.

Expressed another way, the invention provides a device for the administration of a liquid-carried pharmaceutical to a patient comprising means defining a passage for the flow of the liquid during administration thereof characterised by an active pharmaceutical material stabilized in a glassy material that is soluble in the liquid and that forms a coating on supporting means located in the passage so that the glassy material will dissolve in the liquid thereby releasing the pharmaceutical into the liquid as it flows along the path to the patient.

It will be seen that, unlike the prior art, it is advantageous that there is no physico-chemical bonding of the stabilised pharmaceutical material to the supporting structure so as to facilitate the rate of dissolution into the eluant. As the eluant only acts as a solvent for the supported glass and is unrestricted by the need be able to co-exist with the pharmaceutical material for extended periods of time; it becomes possible to use pure water or an aqueous saline as the liquid.

The invention can also be expressed in terms of a method and thus, according to a further aspect of the invention there is provided a device for the administration of a liquid to a patient comprising means defining a passage for the flow of the liquid during administration thereof characterised by an active pharmaceutical material located in the passage so that it will be dissolved or dispersed in the liquid when caused to flow along the path to the patient.

Expressing the method of the invention in another way, the invention provides a method of preparing a pharmaceutical prior to administration to a patient in which a carrier liquid is caused to flow along a passage containing an active ingredient stabilised by a glassy substance so that the agent becomes dissolved or dispersed in the liquid prior to delivery to the patient.

In one preferred embodiment of the invention a syringe is used to flow the liquid through the porous material and out through a needle. However, it is equally possible for the invention to be utilised with other delivery devices such as eye droppers, inhalers for the deep lung, nasal spray inhalers or patch injectors which do not necessarily have a well defined passage for liquid flow.

The supporting surface is preferably defined by a body that is porous to the liquid. This body can be formed of filaments, strands or particles over which the liquid can flow, resulting in dispersion or dissolution of the pharmaceutical material in the liquid as a suspension or in solution. However, other arrangements are possible; for example, a pharmaceutical material could be deposited on a wall that defines a passage for the flow of liquid.

A supporting surface in the form of a sheet has been found to work well, preferably with a supporting structure for the sheet located downstream of it.

So as to comply with guidelines which limit the volume of liquid which is allowed to be injected as part of a vaccination, it is preferable that only a small volume of liquid be used to transfer all of the material supported on the porous body into the liquid. Especially in infants this volume should be less than 1 ml, preferably less than or equal to 0.5 ml which is the standard dose generally accepted for current vaccines. To achieve this it is preferable that the material forming the porous body:

does not become swollen so as to retain the carrier liquid rather than simply allowing it to pass through;

has a large surface area so that it can carry and subsequently dry the pharmaceutical material as a thin layer that quickly dissolves or otherwise disperses;

has a functional pore size, preferably between 1 to 100 microns, more preferably between 3 to 50 microns and most preferably between 6 and 30 microns which does not inhibit the passage of the liquid carrying the pharmaceutical material;

is hydrophilic, or can easily be rendered hydrophilic so that the material forming the glass will exert strong capillarity and draw the glass forming solution, containing the vaccine to be stabilised, widely throughout the porous body so as to ensure the formation of thin glass during drying;

has an innate low affinity for physico-chemical bonding with the active agent;

has a high volume capacity to enable as much active ingredient to be stored on as small a membrane as possible;

does not shed fibres which could be dangerous if injected into the patient.

Examples of suitable porous materials are synthetic plastic materials of which polypropylene and polyester have been found to be particularly suitable. Examples of less suitable porous materials include cellulose, glass fibre and cellulose/glass composites. Examples of unsuitable porous material are nitrocellulose or ion exchange or charged membranes that actively bind the active molecules that constitute the vaccine.

Fibrous structures are preferred as they have, inter alia, a large surface area and so allow a larger volume or loading capacity. The functional pore size is associated with the diameter of a particle that can pass though it. It does not necessary represent the size of the spaces between the fibres but the size of the space as a result of the staggering of spaces between the fibres which form the thickness of the membrane. It is preferable that the glass forms a coating on the fibres so as to define spaces between the fibres whereby the liquid can pass through the spaces dissolving the adjacent glass and so carrying the active ingredient.

A membrane as described above is though to have independent inventive merit and thus according to another aspect of the invention there is provided a pharmaceutical device defining a fibrous body and glassy material stabilising an active ingredient deposited on the fibres, the coated fibres defining spaces between them whereby a solvent can pass through the device dissolving the glassy substance.

Membranes having a functional pores size below 1 micron have demonstrated low recovery rates, where 'recovery rate' is the proportion of the active material that dissolves when a standard volume of water is passed through it using a syringe. For example, membranes with functional pores sizes of 0.22 microns and 0.45 microns have a recovery rate under 30%. There is a trend that as the pore size increases the recovery rate also increases until a limit at around 50 micron pore sizes. Membranes with pores sizes between 10 and 70 microns have all shown recoveries of over 70%, and membranes with 6 micron pore sizes have a recovery rate of around 60%. However, membranes with increased pore sizes above 25 microns and particularly above 30 microns have a lower loading capacity and glasses formed on them often display poorer glass quality. It is believed that glasses formed on membranes with a pore size above 100 microns are of too poor a quality to be useful.

Although membranes having pores sizes between 1 micron and 100 microns are functional, membranes having a pore size between 3 microns and 50 microns are preferred, with pores sizes between 6 microns and 25 microns being most preferable.

So as to inhibit physiochemical bonding between the porous body and the active agent, it maybe necessary that the porous body be treated with a blocking agent before the material is applied to it. Ideally the blocking agent acts to occupy sites where physiochemical bonding would otherwise occur between the porous body and the active agent. Examples of suitable blocking agents are proteins such as caseins or serum albumins, surfactants such as Tween 20 or Tween 80 (RTM of ICI Americas Inc) or preferably polymers such as polyvinyl pyrrolidone.

The fibrous material may if necessary be rendered hydrophilic e.g. by pre-treating it with suitable approved surfactants. Examples of which include those known in the production of emulsions for injection.

It is envisaged that the liquid carrier will normally be aqueous, in which case any glass stabilizer will need to be soluble in the aqueous liquid. Examples of preferred glasses include: amino acid glass, sugar glass, calcium phosphate glass or metal carboxylate glass. Alternative possibilities could be to employ injectable emulsions having an aqueous phase or non-aqueous liquids such as non-toxic oils in which case the solubility of the stabilizing agent will need to be with reference to such alternative liquids.

An example of the invention will now be given with reference to the accompanying drawings in which:—

Figure 1:
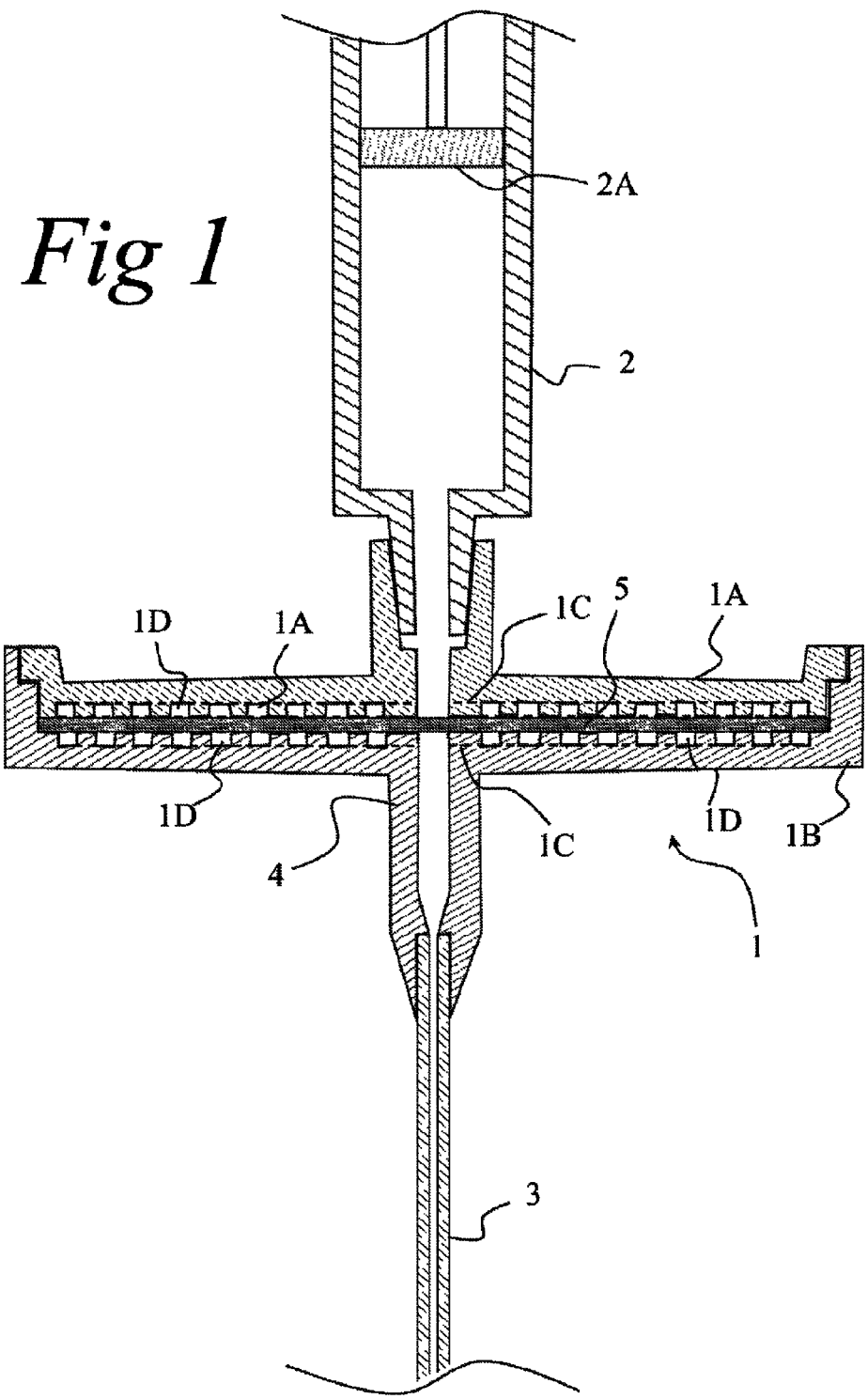
FIG. 1 shows an axial cross-section through an injector embodying the invention.
Figure 2:
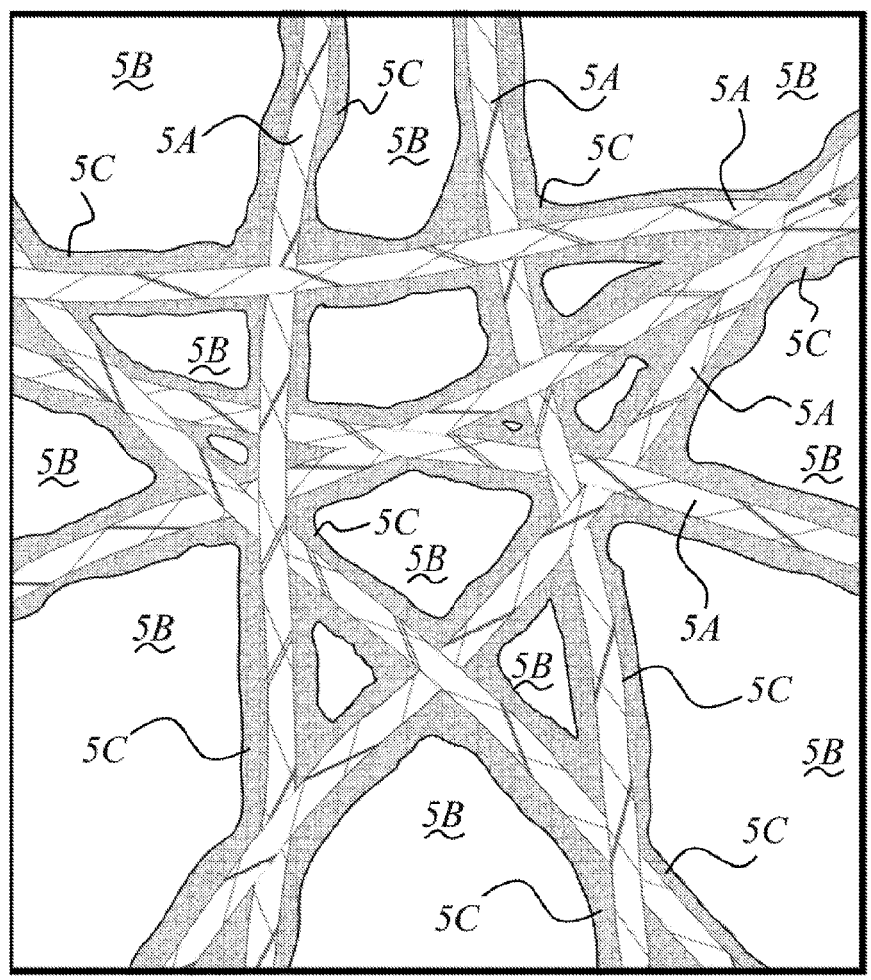
FIG. 2 shows, schematically, a detail of part of a membrane employed in the injector of FIG. 1.
Figure 3:
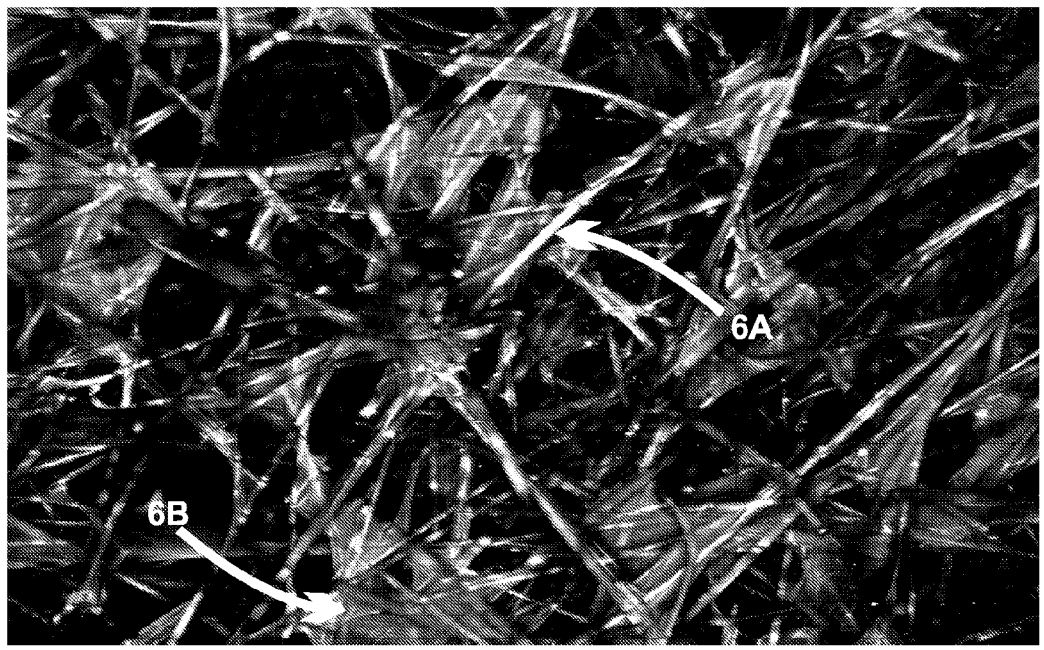
Figure 4:
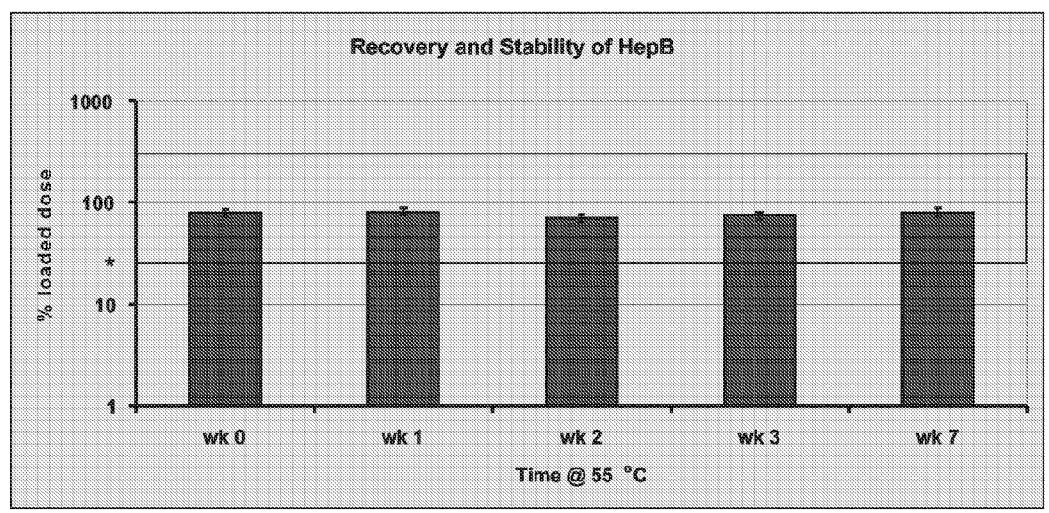

FIG. 3 a confocal microscope optical thin section image of the membrane shown schematically in FIG. 2 where the fibres have been coated by the herein described method with a glassy material containing a fluorescent tracer; and FIG. 4 is a chart illustrating the recovery of stabilised Hepatitis B vaccine stored for various periods of time on a membrane at 55° C. and then flushed through once using 0.5 ml of saline solution;

Referring first to FIG. 1, there is shown a disc-shaped housing 1 connected releasably to the outlet of a conventional syringe 2 and also to a hypodermic needle 3.

The housing 1 is formed from two parts 1A and 1B made of synthetic medically approved plastics and welded together at their peripheries. Each of the housing parts is formed with circular circumferential grooves 1C and straight, radial grooves 1D. The radial and circumferential grooves interlink at their crossing points so as to define an inlet chamber in part 1A and an outlet chamber in part 1B. The inlet chamber allows a flow of liquid from the syringe to spread out so that its cross-section, across the direction of flow, is increased greatly in area. This construction results in the liquid completely and uniformly wetting and flushing through a membrane (to be described later) as the liquid passes from the inlet chamber to the outlet chamber. The outlet chamber has the reverse effect and serves to collect the liquid towards a relatively narrow outlet 4, from whence it is passed into the needle 3 and thence into the patient.

Both the inlet chamber and the outlet chamber are engineered to minimise the dead volume between the syringe and the needle. This design of filter holder is well known to those skilled in the art and is known as an "in line filter." In line filters are supplied commercially by companies such as Millipore, Pall, Sartorius and Whatman.

A circular membrane 5 is held between opposing inner surfaces of the parts 1A and 1B and serves to carry a pharmaceutical material to be injected.

The membrane 5 was prepared as follows starting with a polypropylene based membrane with a functional pore size of 20 microns, known suppliers include Pall Corporation. This membrane 5 material is in the form of a thin sheet with a thickness of around 1 mm.

First the membrane is treated with 100% ethanol followed by 2% (v/v) polyoxyethylene (20) sorbitan monolaurate (Tween 20 dissolved in water) for 20 minutes. The surfactant treated membranes are completely dried at 25° C. This process converts the membrane 5 from a hydrophobic state to hydrophilic state, which allows subsequent loading of the pharmaceutical material.

If a blocking agent is needed a solution of 1% polyvinyl pyrrolidone (PVP) dissolved in water can be passed through the membrane. The membrane can then be washed with pure water to remove any surplus PVP and the membranes dried at 25° C. This process forms a very thin coating, about one molecule thick, of PVP on the membrane fibres to act as a pharmaceutically acceptable blocking agent to prevent unwanted adhesion of the active biological agent onto the membrane fibres.

A solution of 50% by weight (total) of a mixture of monosodium glutamate (MSG) and monosodium aspartate (MSA) in equal molar ratio, is prepared in water and an active biological agent (in this example hepatitis B/aluminium hydroxide adjuvanted vaccine) added in a quantity to give a final MSG/MSA to adjuvant ratio of 40:1.

50 micro liters of the resulting vaccine solution is then loaded onto the centre of the membrane. The solution spreads out by capillary action over most of the area of the membrane and the membrane is allowed to dry at 65° C. overnight in a fan assisted, humidity controlled incubator. These conditions cause the MSG/MSA to form a mixed glass with a residual moisture content between 0.5% to 5% weight by volume and a glass transition temperature of about or over 40° C. The resulting membrane carries 10 micrograms of vaccine bound to 0.57 milligrams of aluminium hydroxide adjuvant, stabilized by 22.8 milligrams of MSG/MSA.

FIG. 2 shows a drawing of a greatly enlarged view of part of the resulting membrane 5. It is formed of a mat of polypropylene fibres 5A having spaces 5B, the size of which may vary enormously, many will have a diameter many times larger than the functional pore size of the membrane. The surface of the fibres carries layer 5C which forms the pharmaceutical substance comprising the above-described mixture of MSG/MSA, vaccine and adjuvant. FIG. 3 is an image of an optical thin section obtained from a scanning confocal microscope. The glassy matrix deposited on the membrane fibres has been rendered fluorescent by the addition of a small quantity of dextran-fluorescein as a placebo vaccine substance prior to drying. This allows visualisation of the glass following laser excitation. The glass appears as thin sheaths coating the fibres of the membrane 6A and occasionally as thin webs between adjacent fibres 6B Each membrane disc 5 is placed in a housing part 1B (FIG. 1) and the two parts 1A and 1B are welded together to form a conveniently packaged component which can be stored and transported without refrigeration because of the stabilizing effect of the MSG/MSA. The entire device is sealed into a moisture-barrier foil pouch (not shown) for storage.

At the point of use, the pouch is opened and the housing 1 is attached to a conventional syringe 2 filled with the appropriate amount, say 0.5 milliliters, of readily available water or saline solution and to a needle 3. On depression of the plunger 2A, the water or saline solution passes into the inlet chamber defined by interlinking grooves 1C and 1D, defined by the housing part 1A, where it spreads out, i.e. the cross-section across the direction of flow increases, so that the solution passes laterally through all parts of the membrane structure 5. As the solution passes through the interstices 5B of the membrane, the glass of the layer 5C dissolves, thus releasing the active vaccine and adjuvant into the water or saline solution. The liquid flow is then collected in the outlet chamber defined by the grooves 1C and 1D of the housing part 1B and passes along the needle 3 from whence it is delivered to the patient. Because the biological material is separated from the solution until immediately before administration, there is no opportunity for deterioration.

The thinness of the membrane; its large area as compared with the cross-sectional area of flow at the inlet and outlet of the housing; and the size of the interstices in the membrane structure; all contribute towards permitting the liquid and the active ingredient carried by it to flow freely through the device and a large proportion of the active material to be effectively dissolved or dispersed into an acceptably small volume of the liquid. Alternatively, a sterilising filter e.g. one with a pore size of 0.45 microns or preferably 0.2 microns can be interposed during manufacture between the syringe end and the membrane 5 on which the vaccine is dried so as to ensure cleanliness and sterility of the liquid water or saline used to re-constitute the vaccine.

FIG. 4 illustrates how effectively the device allows the stabilised active material to be washed from the membrane. There is shown the average recovery rate of Hepatitis B vaccine when 0.5 ml of saline solution is passed through the membrane once. Each bar represents the average recovery from 10 samples stored for 0, 1, 2, 3 and 7 weeks respectively at 55° C. As can be seen the recovery rates are near 100% and the variance between the samples in each group is small.

It will be appreciated that many variations can be made to the described example without departing from the invention as claimed in the appended claims. For example, the vaccine could be replaced by any biological material that would normally be subject to degradation if stored in liquid solution or suspension such as hormones, protein and viral vaccines and genetic material; the MSG/MSA mixture could be replaced by any other soluble stabilising glasses such as pure MSG, other amino acid glasses, sugar glass, calcium phosphate glass, metal carboxylate or mixtures of the above; and the syringe could be replaced by an automated liquid delivery device for mass inoculations.

In an alternative embodiment the liquid could be an emulsion of the oil-in-water or water in oil type and as such the pharmaceutical material could become associated with the aqueous phase of the emulsion as the aqueous phase dissolves the glass. In a further alternative, an oil eluant could be used in conjunction with an oil soluble glass.

As an alternative glass forming process the liquid on the membrane 5 could be frozen and dried in a vacuum (freeze dried).

The invention claimed is:
1. A pharmaceutical device comprising:
a housing comprising an inlet and an outlet; and
a permeable network comprising a fibrous polymeric support coated with a glassy pharmaceutical composition comprising a water-soluble sugar glass and a pharmaceutical agent; and
wherein the permeable network is disposed in the housing and is in fluid communication with the inlet and the outlet; and wherein the pore size of the fibrous polymeric support is between 3 microns and 50 microns.

2. The pharmaceutical device of claim 1, wherein the fibrous polymeric support is composed of polypropylene.

3. The pharmaceutical device of claim 1, wherein the fibrous polymeric support is composed of a polyester.

4. The pharmaceutical device of claim 1, wherein the pore size of the fibrous polymeric support is between 6 microns and 50 microns.

5. The pharmaceutical device of claim 1, wherein the pore size of the fibrous polymeric support is between 6 microns and 25 microns.

6. The pharmaceutical device of claim 2, wherein the pore size of the fibrous polymeric support is between 6 microns and 50 microns.

7. The pharmaceutical device of claim 2, wherein the pore size of the fibrous polymeric support is between 6 microns and 25 microns.

8. The pharmaceutical device of claim 3, wherein the pore size of the fibrous polymeric support is between 6 microns and 50 microns.

9. The pharmaceutical device of claim 3, wherein the pore size of the fibrous polymeric support is between 6 microns and 25 microns.

10. The pharmaceutical device of claim 1, wherein the permeable network further comprises a surfactant layer between the fibrous polymeric support and the coating composed of the glassy pharmaceutical composition.

11. The pharmaceutical device of claim 10, wherein the surfactant layer comprises a surfactant selected from the group consisting of polyoxyethylene (20) sorbitan monolaurate and polyoxyethylene (20) sorbitan monooleate.

12. The pharmaceutical device of claim 1, wherein the permeable network further comprises a layer of polyvinylpyrrolidone between the fibrous polymeric support and the coating composed of the glassy pharmaceutical composition.

* * * * *